US009662408B2

(12) United States Patent
Han et al.

(10) Patent No.: US 9,662,408 B2
(45) Date of Patent: May 30, 2017

(54) BIOCOMPATIBLE FIDUCIAL MARKER USING MULTI-BLOCK COPOLYMERS

(71) Applicants: SAMSUNG LIFE PUBLIC WELFARE FOUNDATION, Seoul (KR); Research & Business Foundation SUNGKYUNKWAN UNIVERSITY, Suwon-si (KR)

(72) Inventors: Young Yih Han, Seoul (KR); Hee Chul Park, Seoul (KR); Doo Sung Lee, Gwacheon-si (KR); Jae Myoung Noh, Seoul (KR); Sang Hee Ahn, Seoul (KR); Hye Young Kim, Seoul (KR); Moon Soo Gil, Anyang-si (KR)

(73) Assignees: SAMSUNG LIFE PUBLIC WELFARE FOUNDATION, Seoul (KR); RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 0 days.

(21) Appl. No.: 14/919,095

(22) Filed: Oct. 21, 2015

(65) Prior Publication Data
US 2016/0106870 A1 Apr. 21, 2016

(30) Foreign Application Priority Data
Oct. 21, 2014 (KR) .......................... 10-2014-0142563

(51) Int. Cl.
*A61K 9/00* (2006.01)
*A61K 49/04* (2006.01)

(52) U.S. Cl.
CPC ................................ *A61K 49/0404* (2013.01)

(58) Field of Classification Search
CPC .................................................. A61K 49/0404
See application file for complete search history.

(56) References Cited

U.S. PATENT DOCUMENTS

| 2008/0234532 A1 | 9/2008 | De Langen et al. | |
| 2011/0142936 A1* | 6/2011 | Campbell | A61L 27/50 424/484 |

OTHER PUBLICATIONS

Fuller et al., "Fiducial markers in image-guided radiotherapy of the prostate," US Oncological Disease. 1(2):75-9 (2006).
(Continued)

*Primary Examiner* — Paul Dickinson
(74) *Attorney, Agent, or Firm* — Clark & Elbing LLP; Susan M. Michaud

(57) ABSTRACT

The present invention relates to a fiducial marker comprising barium sulfate ($BaSO_4$), a solvent, and a polyethylene glycol-poly(aminourethaneurea) multi-block copolymer, as active ingredients. The fiducial marker of the present invention has an effect of significantly remedying disadvantages of image distortion and dose distortion, which are involved in the gold inner marker used in the conventional art. The fiducial marker of the present invention has very limited in vivo mobility, and thus the fiducial marker is maintained at the position at which it has been initially injected. Since the fiducial marker of the present invention is maintained in a sol or liquid state before in vivo injection, and transited into a gel or solid phase after in vivo injection, the injectability of the fiducial marker by an injector syringe is favorable, and the state of the fiducial marker can be controlled into a phase suitable to each site of the therapeutic target.

12 Claims, 11 Drawing Sheets

(56) References Cited

OTHER PUBLICATIONS

Huynh et al., "Injectable block copolymer hydrogels: achievements and future challenges for biomedical applications," Macromolecules. 44(17):6629-36 (2011).
Huynh et al., "Synthesis and characterization of poly(amino urea urethane)-based block copolymer and its potential application as injectable pH/temperature-sensitive hydrogel for protein carrier," Polymer. 53(19):4069-75 (2012).
Shim et al., "Poly(D,L-lactic acid-co-glycolic acid)-b-poly(ethylene glycol)-b-poly (D,L-lactic acid-co-glycolic acid) triblock copolymer and thermoreversible phase transition in water," J Biomed Mater Res. 61(2):188-96 (2002).

* cited by examiner

BIOCOMPATIBLE FIDUCIAL MARKER USING MULTI-BLOCK COPOLYMERS

BACKGROUND OF THE INVENTION

1. Field of the Invention

The present invention relates to a fiducial marker using a biodegradable multi-block copolymer.

2. Description of the Prior Art

In external-beam radiotherapy, the degree of correspondence between the radiation beam angle and a target object is important in order to provide an accurate dose to a tumor location as much as possible. Especially, in the case of patients with lung cancer or liver cancer strongly affected by respiration, it is difficult to accurately apply radiation to tumors due to motion of organs due to the respiration. Therefore, it is important to establish the therapeutic plan considering the motion of tumors due to respiration, in order to increase the success rate of radiotherapy on moving organs. At the time of actual treatment, the accuracy of radiotherapy is improved by real-time tracing the motion of a marker inserted in the human body to accurately and promptly trace the motion of organs.

For these aims, gold markers easily recognizable on images are used in actual radiotherapy, but a metal material has disadvantages in that X-rays increase image distortion and dose distortion. The image distortion makes it hard to determine a target and surrounding organs on images, causing inaccuracy at the time of delineating a target and a region of interest (ROI), and the determination of the marker position is actually affected by radiographic visibility and computed tomography (CT) image artifacts, so the marker position may be shown differently.

As for proton therapy, the therapy range by Bragg peak is important. However, according to existing study results, the dose distortion occurs around a gold marker when the direction of the proton beam is set to pass through the gold marker. In order to reduce such dose distortion, researches on the diminishment in the dose distortion through the mixing of gold nanoparticles and bone cement has been conducted.

Accordingly, the present invention aims to develop a fiducial marker that has excellent identifiability on medical images and minimized mobility in biological tissues by combining a contrast agent material and a biodegradable polymer material.

Throughout the entire specification, many papers and patent documents are referenced and their citations are represented. The disclosure of cited papers and patent documents are entirely incorporated by reference into the present specification, and the level of the technical field within which the present invention falls and details of the present invention are explained more clearly.

SUMMARY OF THE INVENTION

In order to solve the problems, the present inventors have researched and endeavored to develop a fiducial marker using a biodegradable multi-block copolymer. As a result, the present inventors have successfully prepared a barium sulfate ($BaSO_4$) fiducial marker by dispersing barium sulfate ($BaSO_4$) in a polyethyleneglycol-poly(aminoureaurethane) multi-block copolymer solution, and have experimentally proved that the prepared barium sulfate ($BaSO_4$) fiducial marker has excellent injectability, minimizes image distortion and dose distortion, has limited in vivo mobility, and is degraded in vivo, and thus have completed the present invention.

Therefore, an aspect of the present invention is to provide a fiducial marker using a biodegradable multi-block copolymer.

Other purposes and advantages of the present disclosure will become more obvious with the following detailed description of the invention, claims, and drawings.

In order to accomplish these objects, there is provided a fiducial marker, including: (i) barium sulfate ($BaSO_4$); (ii) a solvent: and (iii) a polyethylene glycol-poly(aminoureaurethane) multi-block copolymer, as active ingredients.

As used herein, the term "fiducial marker", in the largest sense, means an object placed in the field of view of an imaging system, for use as a point of reference of a measure.

The fiducial marker of the present invention is prepared by dissolving a polyethyleneglycol-poly (aminoureaurethane) multi-block copolymer in a solvent to prepare a polymer solution, and adding and dispersing barium sulfate ($BaSO_4$) in the polymer solution.

In the fiducial marker of the present invention, barium sulfate ($BaSO_4$) is used as a contrast component. Barium sulfate ($BaSO_4$), which is a white powder, has desirable physical properties as a contrast agent since it is mostly insoluble in water, ethanol, ether, and chloroform, and also insoluble in acid and alkali, and thus is neither dissolved in gastric fluid or serous fluid nor absorbed into digestive tracts.

According to another embodiment of the present invention, the content of barium sulfate ($BaSO_4$) is 1-wt %, more preferably 5-30 wt %, and still more preferably 10-30 wt % in the fiducial marker of the present invention. Less than 10 wt % of barium sulfate ($BaSO_4$) in the fiducial marker is difficult to identify on diagnostic X-ray images, and more than 30 wt % may cause image distortion (streak artifacts) due to barium sulfate ($BaSO_4$).

In the fiducial marker of the present invention, the polyethyleneglycol-poly(aminoureaurethane) multi-block copolymer is used as a carrier for barium sulfate ($BaSO_4$). The polyethyleneglycol-poly(aminoureaurethane) multi-block copolymer safely delivers barium sulfate ($BaSO_4$) to a target site in the living body while enclosing the barium sulfate ($BaSO_4$), and then forms a fiducial marker at the target site.

According to another embodiment of the present invention, the polyethyleneglycol-poly(aminoureaurethane) multi-block copolymer has a repeat unit represented by chemical formula 1:

[Chemical formula 1]

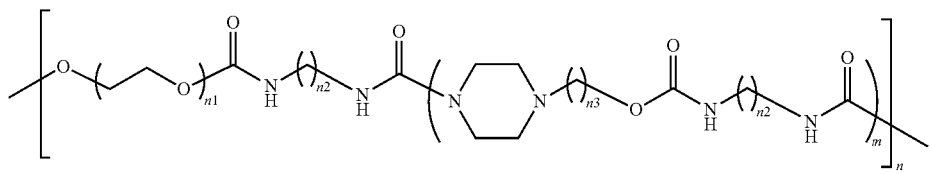

wherein in chemical formula 1, n1 is an integer of 7 to 50; n2 is an integer of 2 to 8; n3 is an integer of 1 to 10; and m is an integer of 2 to 6.

According to another embodiment of the present invention, the polyethyleneglycol-poly(aminoureaurethane) multi-block copolymer represented by chemical formula 1 has a molecular weight of 15,000 g/mol to 25,000 g/mol.

A multi-block copolymer having a molecular weight of less than 15,000 g/mol may not exhibit a sol-gel transition behavior depending on the temperature and pH change under in vivo physiological conditions, and a multi-block copolymer having a molecular weight of more than 25,000 g/mol is difficult to exhibit a sol-gel transition behavior under in vivo physiological conditions.

In addition, the molecular weight ratio of hydrophilic blocks and hydrophobic blocks is preferably 1:2 to 1:4 in the polyethyleneglycol-poly (aminoureaurethane) multi-block copolymer represented by chemical formula 1. In the above, block n1 always serves as a hydrophilic block and block n2 always serves as a hydrophobic block, whereas block n3 serves as a hydrophilic block in an ionized state and a hydrophobic block in a non-ionized state.

According to another embodiment of the present invention, n2 is 6 and n3 is 2, in chemical formula 1 above.

In the fiducial marker of the present invention, the content of the polyethyleneglycol-poly(aminoureaurethane) multi-block copolymer may be appropriately selected by a person skilled in the art, and is preferably 1-50 wt %, more preferably 1-30 wt %, and still more preferably 1-20 wt %.

According to another embodiment of the present invention, the polyethyleneglycol-poly (aminoureaurethane) multi-block copolymer of the fiducial marker of the present invention has a biodegradable property in which it is degraded in vivo over time after in vivo injection.

In the fiducial marker of the present invention, the solvent serves as a medium in which the polyethyleneglycol-poly (aminoureaurethane) multi-block copolymer is dissolved or dispersed.

According to another embodiment, the solvent in the fiducial marker of the present invention is a buffer solution, and buffered saline may be preferably used. The buffered saline includes, but is not limited to, a phosphate buffered saline (PBS) solution, a tris buffered saline (TBS) solution, or a borate buffered saline (BBS) solution.

The content of the solvent in the fiducial marker of the present invention may be appropriately selected by a person skilled in the art, and is preferably 1-95 wt %.

Herein, one of the largest physical properties of the fiducial marker of the present invention is sol-gel transition depending on the temperature and pH range.

According to another embodiment of the present invention, the fiducial marker of the present invention is present in a sol or liquid phase at pH of less than 7.0 and a temperature range of 15-25° C., and present in a gel or sold phase at pH of 7.0-7.5 and a temperature range of 30-40° C.

According to another embodiment of the present invention, the fiducial marker of the present invention has an injection type in which it is injected in vivo in a sol or liquid phase.

According to another embodiment of the present invention, the fiducial marker of the present invention is hardened in vivo to be in a gel or solid phase after in vivo injection.

The fiducial marker of the present invention has excellent in vivo injectability through injection by maintaining the sol or liquid phase thereof under room temperature conditions before in vivo injection, and satisfies physical properties required as a fiducial marker by maintaining the gel or solid phase thereof under in vivo temperature and pH conditions. That is, the fiducial marker is maintained in a sol or liquid phase, and thus can be safely delivered into the body without a blockage in the injection needle, and the fiducial marker is transited into a gel or solid phase in the body, and thus has limited in vivo mobility, satisfying physical properties as a fiducial marker.

According to an embodiment of the present invention, the fiducial marker of the present invention is used to display the position of the diseased area in the body at the time of radiotherapy.

Radiotherapy is a treatment method in which, based on diagnostic images for a tumor, the therapeutic radiation is intensively applied to the tumor to kill tumor cells. Since normal tissues around the tumor, excluding the tumor, need to be protected from the therapeutic radiation so as to minimize side effects due to the radiation at the time of radiotherapy, the technique of visualizing the position of the tumor is very important to raise therapeutic effects in radiotherapy.

The fiducial marker for the use of radiotherapy needs to satisfy the following principal requisites. First, the fiducial marker should have excellent identifiability in the diagnostic X-ray area. Second, the distortion of the dose of therapeutic radiation transmitted to the tumor needs to be minimized. Third, when the therapeutic plan based on computed tomography (CT) is established, the distortion of computed tomography (CT) images needs to be minimized. Fourth, the motion of the fiducial marker needs to be minimized in the human body.

The fiducial marker used in the conventional art for accurate visualization of the position of the tumor was particles of metal, such as gold or titanium, and the position of the diseased part was confirmed through diagnostic X-ray images after the metal particles are infused into the tumor. However, the use of such a metal material as a component of the fiducial marker is problematic due to large increases in dose distortion and image distortion.

At the time of radiotherapy, the image distortion by the fiducial marker makes it difficult to differentiate cancer tissues from surrounding normal tissues, causing an increase in the inaccuracy at the time of setting a target and a region of interest (ROI) for therapeutic plans.

At the time of radiotherapy, the dose distortion may make it difficult to calculate the accurate dose in the therapeutic plan establishment procedure, prevent the delivery of the dose following the therapeutic plan to the target site, and cause the delivery of unnecessary dose to the normal tissues. Meanwhile, the use of the fiducial marker containing a metal material, of the conventional art, has been reported to cause the dose distortion in the periphery of the metal material.

The fiducial marker of the present invention significantly improves the image distortion and the dose distortion compared with the fiducial marker using a metal material, of the conventional art.

The fiducial marker using barium sulfate ($BaSO_4$) and a polyethyleneglycol-poly(aminoureaurethane) multi-block copolymer solution, of the present invention, exhibited sufficient identifiability on computed tomography (CT) and X-ray images, regardless of the use of smaller markers, compared with metal markers.

The fiducial marker using barium sulfate ($BaSO_4$) and a polyethyleneglycol-poly(aminoureaurethane) multi-block copolymer solution, of the present invention, significantly reduced the dose distortion, compared with the metal marker using gold, stainless steel, and titanium.

The injectable dose of the fiducial marker of the present invention may be appropriately selected by a person skilled art.

According to another embodiment of the present invention, the fiducial marker of the present invention has a diameter of 0.1-5.0 mm, more preferably 0.1-4.0 mm, still more preferably 0.5-3.0 mm, and most preferably 0.5-2.0 mm.

According to another embodiment of the present invention, the fiducial marker of the present invention has a volume in the range of 0.001-0.1 cm$^3$.

According to another embodiment of the present invention, the fiducial marker of the present invention has viscosity of 1 Pa·s to 104 Pa·s.

According to a specific embodiment of the present invention, as a result of preparing and using a fiducial marker having a diameter of 2 mm, a volume of 0.042 cm$^3$, and viscosity of 104 Pa·s or less, the identifiability of the fiducial marker of the present invention was high, and the degree of image distortion was minimized.

According to another embodiment of the present invention, the fiducial marker of the present invention showed a 90% or more reduction in the degree of image distortion, compared with the metal fiducial marker.

According to another embodiment of the present invention, the fiducial marker of the present invention showed a maximum 11.26% reduction in the degree of dose distortion, compared with the metal fiducial marker.

In the present invention, the degree of dose distortion may be determined by subtracting, from dose values (area part) of the reference graph, dose values thereof of the distorted graph.

BRIEF DESCRIPTION OF THE DRAWINGS

The above and other objects, features, and advantages of the present invention will be more apparent from the following detailed description taken in conjunction with the accompanying drawings, in which.

DETAILED DESCRIPTION OF THE PREFERRED EMBODIMENTS

Figure 1:
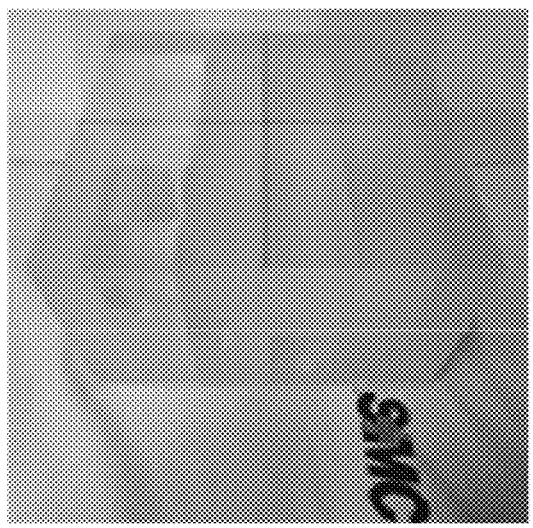
FIG. 1 shows images of a phantom (A) and a mouse cage (B), manufactured of acryl.
Figure 1:
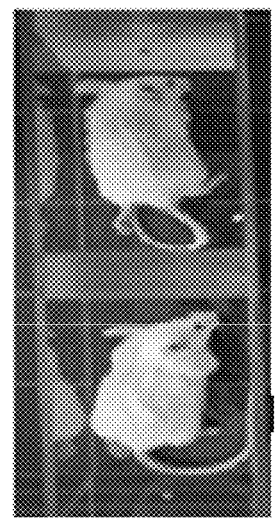
Figure 2:
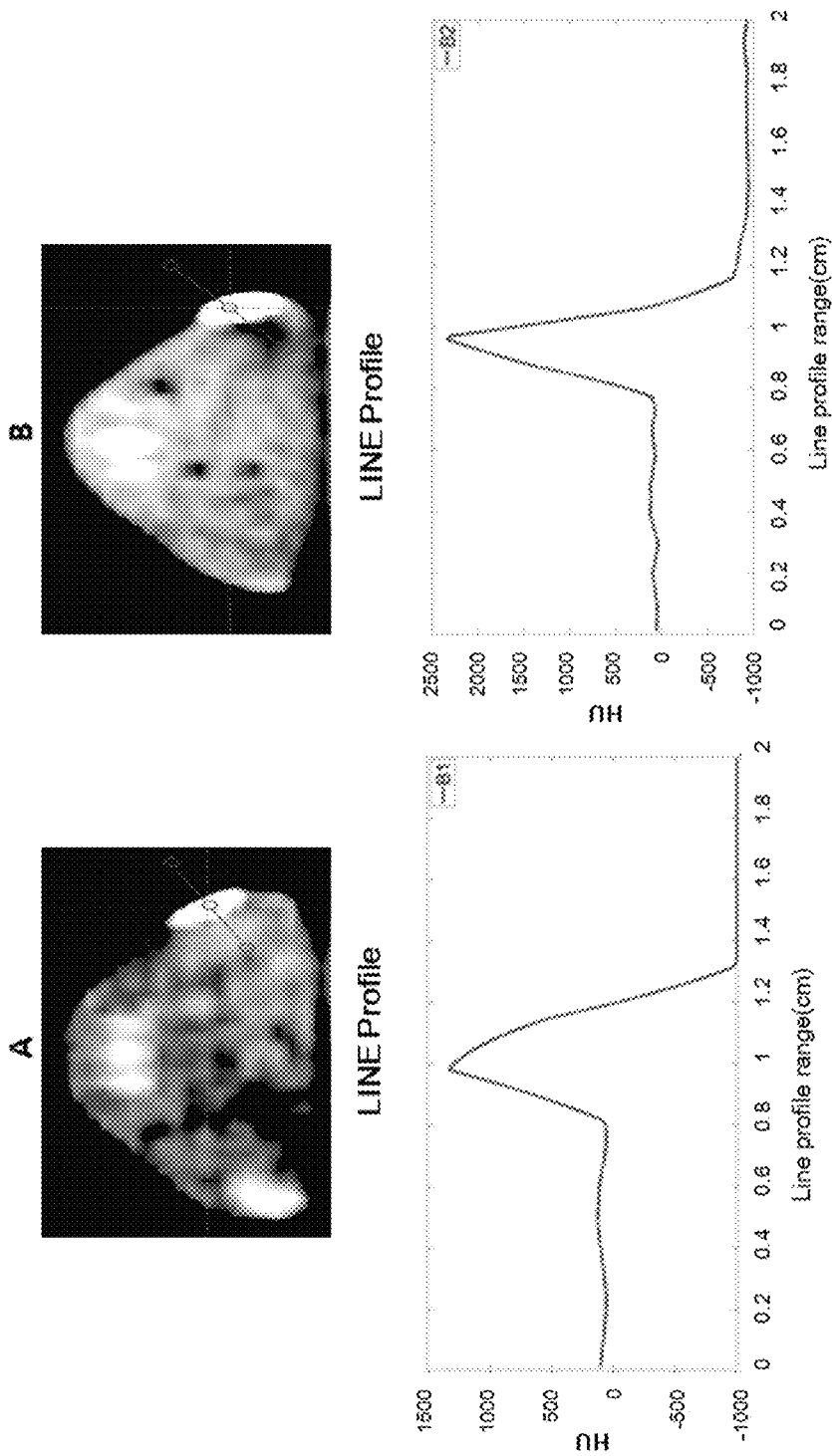
FIG. 2 shows cone-beam computed tomography (CBCT) images and line profile diagrams of barium sulfate (BaSO$_4$) markers. Panel A shows a cone-beam computed tomography (CBCT) image and a line profile diagram of a mm-sized barium sulfate (BaSO$_4$) 10 wt % marker (B1 marker). Panel B shows a cone-beam computed tomography (CBCT) image and a line profile diagram of a 2 mm-sized barium sulfate (BaSO$_4$) 20 wt % marker (B2 marker)

Hereinafter, the present invention will be described in detail with reference to examples. These examples are only for illustrating the present invention more specifically, and it will be apparent to those skilled in the art that the scope of the present invention is not limited by these examples.

EXAMPLES

Materials and Methods

Materials

Polyethylene glycols (PEG), 2-hydroxyethyl piperazine, 1,6-diisocyanato hexamethylene, dibutyltin dilaurate (DBTL), anhydrous chloroform, phosphate buffered saline (PBS), and barium sulfate (BaSO$_4$) were obtained from Sigma-Aldrich (St. Louis, Mo., USA). Hydrochloric acid (HCl), sodium hydroxide (NaOH), and diethyl ether were obtained from Samchun Co. (Seoul, Korea).

Preparation of Barium Sulfate (BaSO$_4$) Markers

Barium sulfate (BaSO$_4$) markers were prepared based on the polyethyleneglycol-poly(aminoureaurethane) ([PEG-PAUU]x) block copolymer (C. T. Huynh, Q. V. Nguyen, S. W. Kang, D. S. Lee, Polymer 2012, 53, 4069), and the synthesis of the copolymer was performed according to the disclosure of literature (Cong Truc Huynh et al., Polymer 53, 2012, 4069-4075; Cong Truc Huynh et al., Macromolecules 2011, 44, 6629-6636). The barium sulfate (BaSO$_4$) marker, which is an X-ray contrast agent, was prepared by diffusing and penetrating barium sulfate (BaSO$_4$) in the synthesized [PEG-PAUU]x block copolymer. That is, the barium sulfate (BaSO$_4$) marker was prepared by sequentially mixing the [PEG-PAUU]x block copolymer as a carrier, and phosphate buffered saline (PBS) as a solvent. First, the synthesized [PEG-PAUU]x block copolymer was dissolved in the phosphate buffered saline (PBS) to give 10 wt % under conditions of 20° C. and pH 6.0, to form a sol in a liquid phase, and then barium sulfate (BaSO$_4$), which is an X-ray contrast, was added to the prepared sol to be dispersed in the sol. Two kinds of barium sulfate (BaSO$_4$) markers having barium sulfate (BaSO$_4$) contents of 10 wt % and 20 wt %, respectively, were prepared. The barium sulfate (BaSO$_4$) marker having a barium sulfate (BaSO$_4$) content of 10 wt % designated by B1 was differentiated from the barium sulfate (BaSO$_4$) marker having a barium sulfate (BaSO$_4$) content of 20 wt % designated by B2.

In Vitro Sol-Gel Transition Measurement

The sol-gel transition measurement was performed on the synthesized barium sulfate ($BaSO_4$) markers B1 and B2 materials in a solution state, through a tube inversion method. The synthesized [PEG-PAUU]x block copolymer was adjusted to pH=1 using 5 N NaOH and 5 N HCl, and completely dissolved in phosphate buffered saline (PBS) for 5 h to give a concentration of 10 wt %. Then, the prepared polymer solution was again adjusted to pH=6.0 at 20° C. and then dispensed in 4 ml tubes. The barium sulfate ($BaSO_4$) was added to the prepared [PEG-PAUU]x block copolymer solutions to give concentrations of 10 wt % (B1) and 20 wt % (B2), respectively, and then dispersed for 1 h using a sonicator (ULSSO TECH, Sonosmasher). Again, the respective tubes were adjusted to a desired pH value, and then stabilized at 2° C. for 12 h. The respective tubes were fixed to a temperature-adjustable water bath, and then the changes of the solutions depending on the temperature change were observed while the temperature was slowly raised from 0° C. to 90° C. The sol-gel transition measurement was conducted using a tube inversion method for 1 min at each temperature.

Rheological Measurement

A dynamic mechanical analyzer (Bohlin Rotational Rheometer) was used to determine the viscosity change of each barium sulfate ($BaSO_4$) marker solution depending on the barium sulfate ($BaSO_4$) concentration. Oscillation mode with controlled conditions of 0.4 Pa and 1 rad/s frequency was used. The variation of the viscosity was observed by loading the barium sulfate ($BaSO_4$) marker solutions on 20-diameter plates, preparing samples with a gap of 250 mm, and then slowly increasing the temperature from 0° C. to 60° C.

In Vivo Gel Formation and Degradation of Barium Sulfate ($BaSO_4$)

Male Sprague-Dawley (SD) rats (Hanlim Experimental Animal Laboratory, Seoul, Korea) were used for the in vivo experiments. The rats (5-6 weeks old, average body weight 200 g) were used, and managed in accordance with the National Institutes of Health (NIH) guide lines for the care and use of laboratory animals.

In order to investigate the injectability through injection, in vivo gelation, and gel stability of the barium sulfate ($BaSO_4$) markers, 200 μl of B1 marker and B2 marker with pH 5.8 were injected subcutaneously into the back of the male SD rats. After the injection, the rats were sacrificed according to the time up to the maximum 4 months, and the gel morphology was observed. In order to investigate the in vivo degradation over time, the rats to which the barium sulfate ($BaSO_4$) markers were injected were sacrificed according to the time, and the gel size was measured. In addition, the gel was freeze-dried, and then the weight of the remaining gel was calculated through comparison with the gel state at the time of initial injection, thereby analyzing biodegradability.

Phantom

In order to insert a cage housing mice into a phantom simulating the human stomach, the phantom was fabricated to have a similar size to the human stomach. The phantom with a size of 30 cm×30 cm×18 cm was fabricated using polymethacrylicacidmethyl (PMMA) (FIG. 1). The cage was separated into two spaces, in which two mice were housed for each. In order to display the marker identifiability according to the position in the abdomen, marker identifiability in the anterior-posterior direction and lateral direction, and the image variation according to the depth in the human body, the cages were fabricated in a terraced form with a depth difference of 2.6 cm-15.4 cm from the surface and a depth difference of 4.2 cm between the cages.

Mice

A total of 40 BALB/C mice (5 weeks old) were experimented on a barium sulfate ($BaSO_4$) 10 wt % marker (B1 marker) group and a barium sulfate ($BaSO_4$) 10 wt % marker (B2 marker) group with 20 mice for each group. The barium sulfate ($BaSO_4$) markers were subcutaneously injected into the back of the right leg using an injection syringe. The amounts of injection were 10 μl (Ø 1.0 mm) and 20 μl (Ø 2.0 mm), and the mice were differentiated by punching the ear.

Optimal Image Conditions Values

The cages housing anesthetized mice were located inside the phantom, and then imaged using image apparatuses installed at the linear accelerator for treatment in the order of cone-beam computed tomography (CBCT), an On-Board Imager, which is an X-ray orthogonal imaging system, and fluoroscopy. The variations of the markers were observed while eleven experiments were conducted every two weeks for five months. Bolus containing the markers were inserted into a solid phantom (270 cm×180 cm×180 cm) fabricated for intensity modulated radiation therapy, and then optimal image condition values for B1 marker and B2 marker were obtained. The sizes of the markers were Ø 1.0 mm and Ø 2.0 mm, which were smaller than 4 mm, the size of the commercialized gold marker. Cone-beam computed tomography (CBCT) was reconstituted with a slice thickness of 1.0 mm, and imaging was conducted in the anterior-posterior direction and lateral direction for OBI and fluoroscopy.

Evaluation on Image Distortion and Dose Distortion

In order to evaluate the degree of image distortion, a gold marker and a barium sulfate ($BaSO_4$) marker were contained in the boluses, and then housed in the phantom cage, followed by computed tomography (CT) imaging for analysis. For analysis of image distortion, the degree of image distortion was evaluated by setting a region of interest (ROI) in the periphery of each of the markers to 20×20 pixels (15.6 mm×15.6 mm) and then analyzing the distribution of the histogram, excluding each marker itself.

In order to investigate the degree of dose distortion in the proton therapy, Monte Carlo computer simulation made based on Geant 4 was conducted. The degrees of dose distortion of gold, stainless steel, titanium, and barium sulfate ($BaSO_4$) were evaluated in the same conditions. Cylindrical markers of gold, stainless steel, titanium, and barium sulfate ($BaSO_4$), which have the same size (diameter: 1 mm, length: 3 mm) as a gold marker (diameter: 1 mm, length: 3 mm) actually used in the radiotherapy, were fabricated, and a proton beam was allowed to pass through the respective markers to compare the degree of distortion therebetween. Each of the markers was located inside the virtual phantom of polymethacrylicacidmethyl (PMMA), having a similar size to the human abdomen such that the marker was located in two direction, parallel and perpendicular to the proton beam direction, and then the proton beam was allowed to pass therethrough to compare the degree of dose distortion through computer simulation.

Results

Barium Sulfate ($BaSO_4$) Marker Images

The barium sulfate ($BaSO_4$) marker could be identified on cone-beam computed tomography (CBCT), On-Board Imager (OBI), and fluoroscopy images, and the degree of identification was verified based on the cone-beam computed tomography (CBCT) image. The identifiability of the barium sulfate ($BaSO_4$) marker was high on the cone-beam computed tomography (CBCT) image, and it was verified that the marker was formed in an irregular shape but not a symmetric sphere shape.

Figure 3:
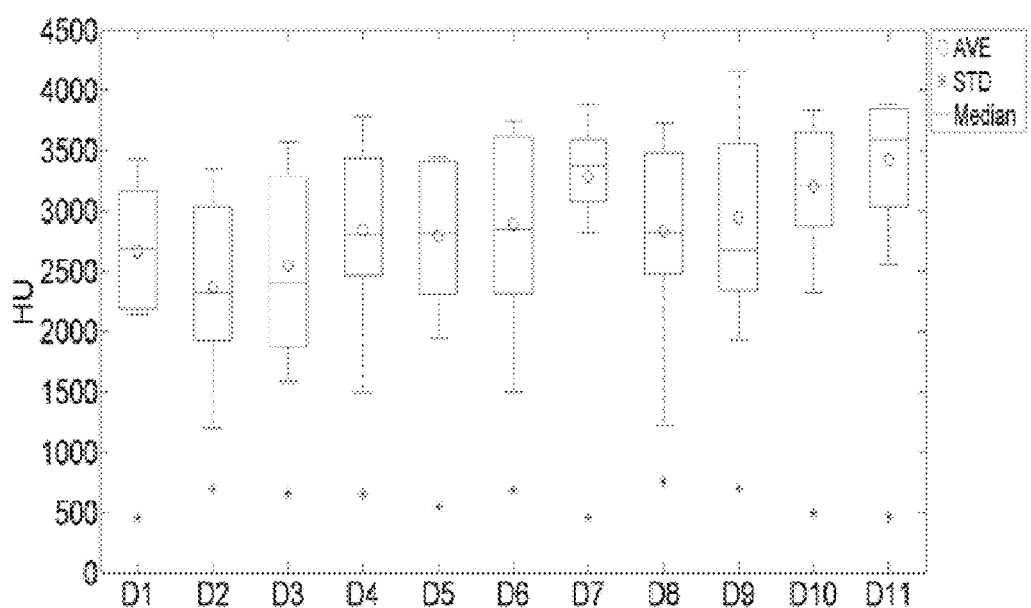
FIG. 3 shows a graph illustrating the maximum brightness intensity over time, of the 2 mm-sized barium sulfate (BaSO$_4$) 20 wt % marker, in terms of Hounsfield unit (HU)
Figure 4:
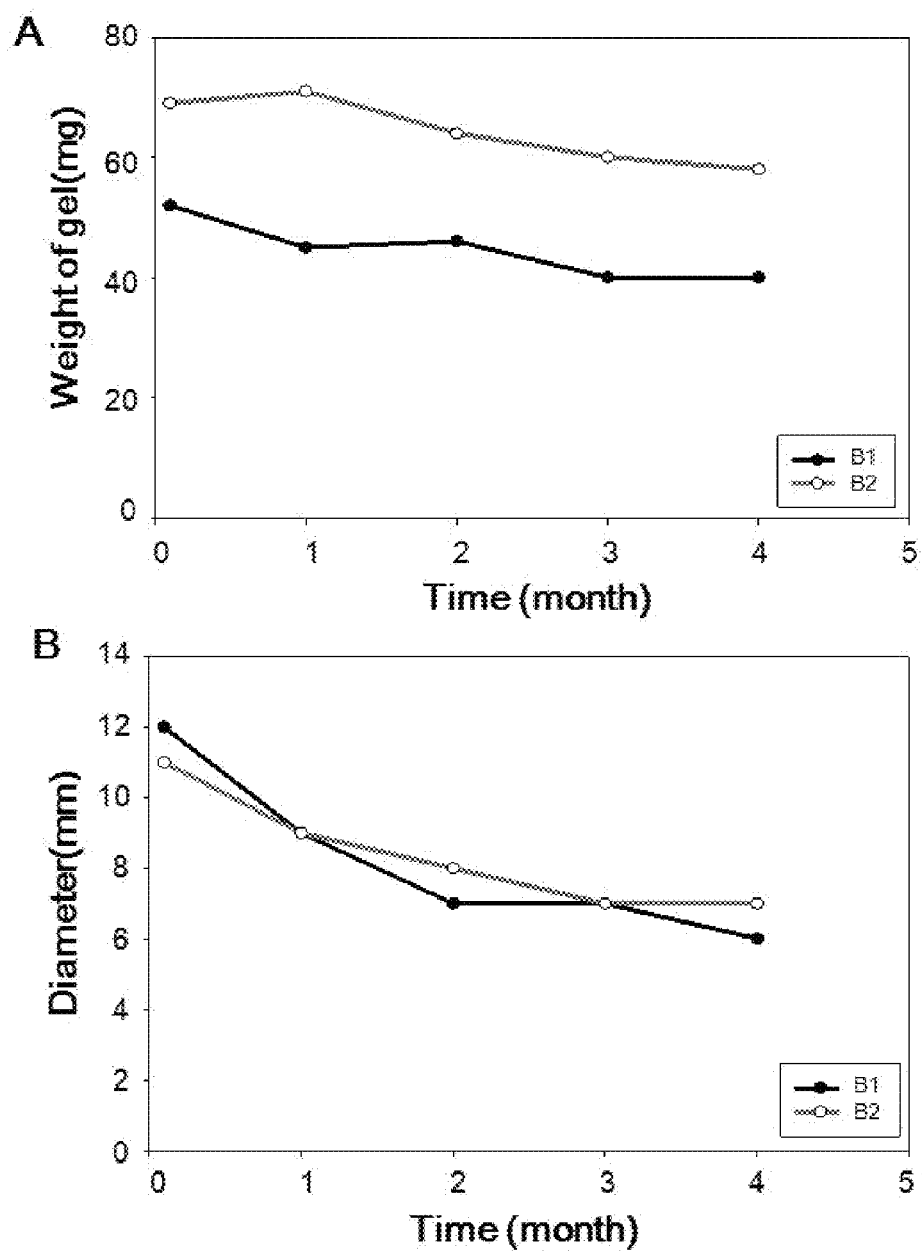
FIG. 4 shows graphs illustrating the changes in weight (panel A) and diameter (panel B) of gels in order to analyze biodegradability over time, of the barium sulfate (BaSO$_4$) 10 wt % marker (B1 marker) and barium sulfate (BaSO$_4$) 20 wt % marker (B2 marker)

Eclipse (version 10.1), which is a commercialized radiotherapy planning system for imaging and analysis, was used. The differentiation on the cone-beam computed tomography (CBCT) image was conducted using naked eye differentiation and the line profile, so that the barium sulfate (BaSO$_4$) marker was differentiated from the surrounding tissues using a profile value of ≥1000. In order to verify the degree of absorption, the maximum brightness intensity of the marker on the image was measured through conversion into gray scale and Hounsfield Unit (HU). As a result of measuring the variation degree of the 2 mm-sized marker of the barium sulfate (BaSO$_4$) 20 wt % B2 marker, which is identifiable group on all the images, at the interval of two weeks, the brightness intensity value showed an increase trend over time in the gray scale and Hounsfield unit (HU) (FIG. 3). It is supposed that these results show that the phosphate buffered saline (PBS) solution constituting the marker, and the polymer as a carrier, were degraded and barium sulfate (BaSO$_4$) was agglomerated, and as a result, the brightness intensity was high on the cone-beam computed tomography (CBCT) image.

Figure 5:
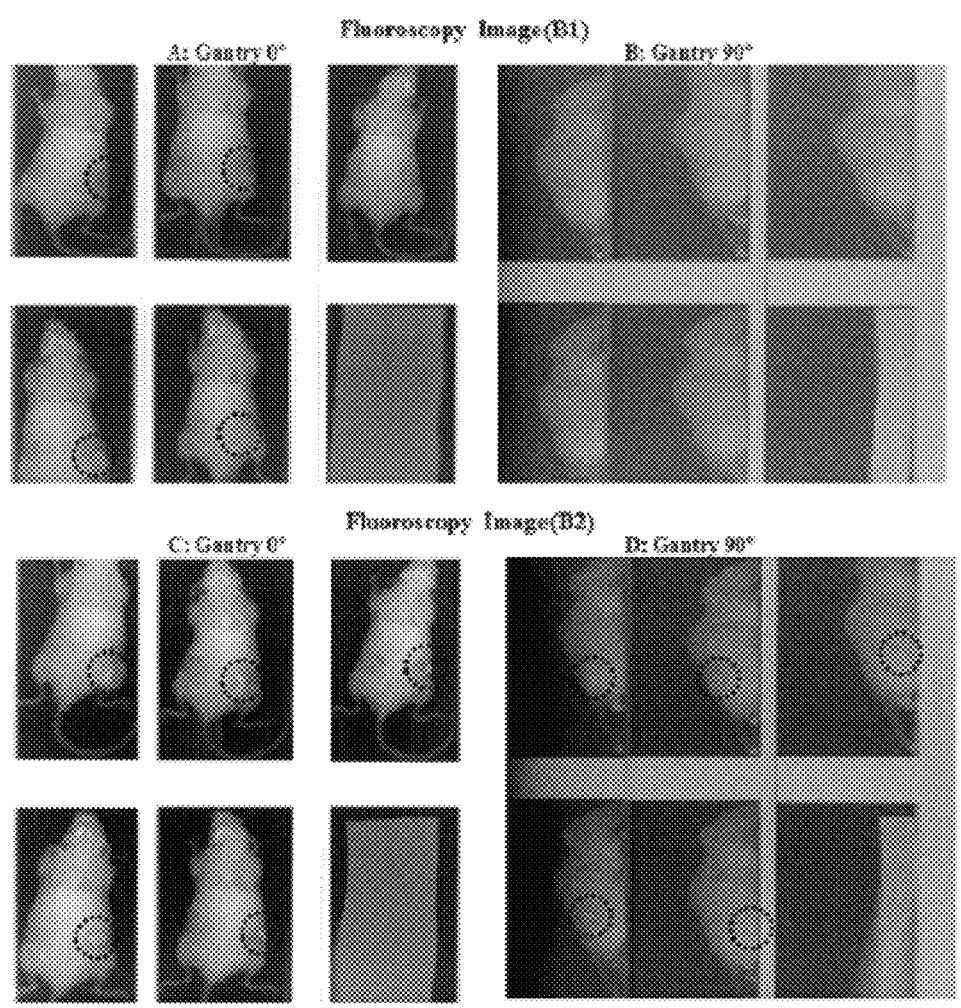
FIG. 5 shows fluoroscopy images of the barium sulfate (BaSO$_4$) 10 wt % marker (B1 marker) and barium sulfate (BaSO$_4$) 20 wt % marker (B2 marker). B2 2 mm mouse A: Gantry 0° Anterior-Posterior direction, B: Gantry 90° Lateral direction, B2 1 mm mouse C: Gantry 0° Anterior-Posterior direction, D: Gantry 90° Lateral direction.

For the On-Board Imager (OBI) and fluoroscopy, the identification of the marker was easier in the anterior-posterior direction rather than the lateral direction, and the identifiability was high in B2 marker having a higher barium sulfate (BaSO$_4$) content and the 2 mm-sized marker (table 1 and FIG. 5). These results mean that the 2 mm-sized barium sulfate (BaSO$_4$) 20 wt % B2 marker was more suitable as a marker.

TABLE 1

| Identifiability | High | Low |
| --- | --- | --- |
| Barium sulfate (BaSO4) marker | B2 | B1 |
| Size | 2 mm | 1 mm |
| Gantry rotation | 0° (Anterior-Posterior) | 90° (Lateral) |
| HU | 1500> | 1500< |

Figure 6:
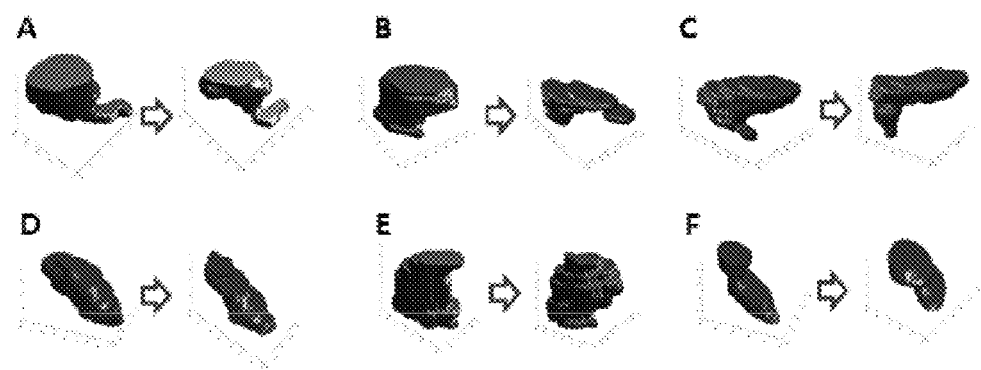
FIG. 6 shows 3D reconstitution images of the size change on cone-beam computed tomography (CBCT) D0 (imaging immediately after marker injection) image and D11 (last imaging) in order to compare the size change among barium sulfate (BaSO$_4$) markers. A: barium sulfate (BaSO$_4$) 10 wt % (B1), 1 mm-sized, No. 5 mouse; B: barium sulfate (BaSO$_4$) 10 wt % (B1), 2 mm-sized, No. 3 mouse; C: barium sulfate (BaSO$_4$) 10 wt % (B1), 1 mm-sized, No. 1 mouse; D: barium sulfate (BaSO$_4$) 20 wt % (B2), 2 mm-sized No. 6 mouse; E: barium sulfate (BaSO$_4$) 20 wt % (B2), 2 mm-sized, No. 8 mouse; F: barium sulfate (BaSO$_4$) 20 wt % (B2), 2 mm-sized No. 2 mouse.
Figure 7:
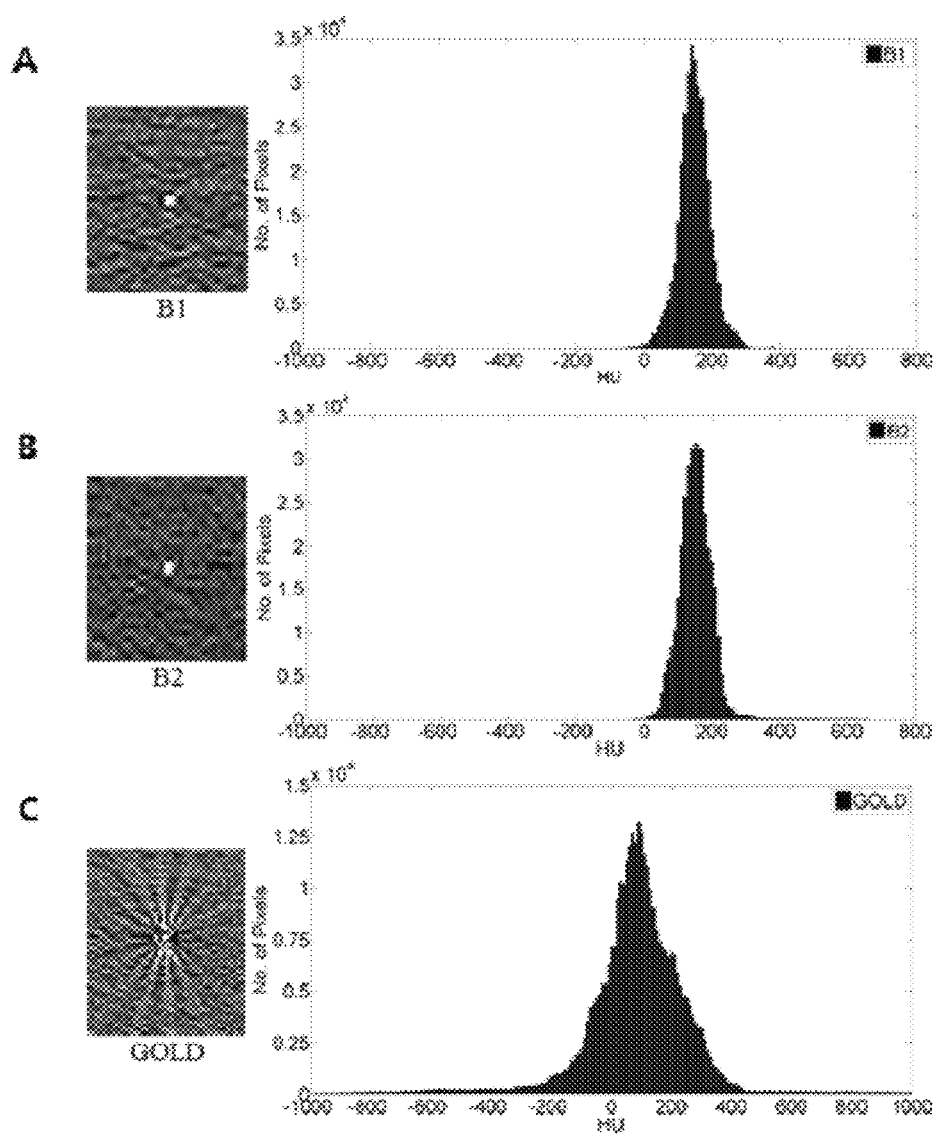
FIG. 7 shows area profile analysis images of fiducial markers. A: Area histogram of barium sulfate (BaSO$_4$) 10 wt % (B1); B: area histogram of barium sulfate (BaSO$_4$) 20 wt % (B2); C: area histogram of gold marker.
Figure 8A:
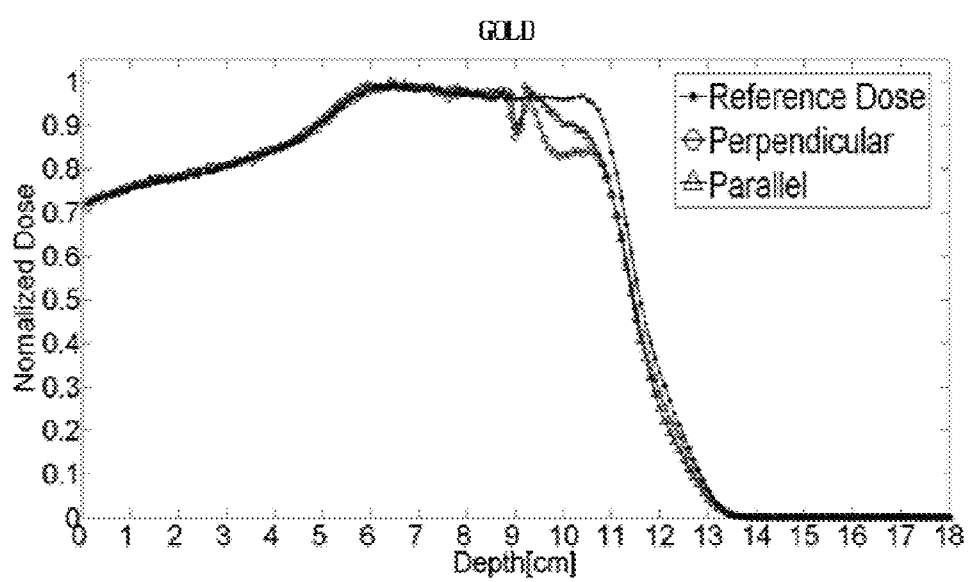
FIGS. 8a to 8d are Monte Carlo Simulation analysis graphs for investigating the degree of dose distortion of gold, stainless steel, titanium, and barium sulfate (BaSO$_4$) fiducial marker materials, respectively.
Figure 8B:
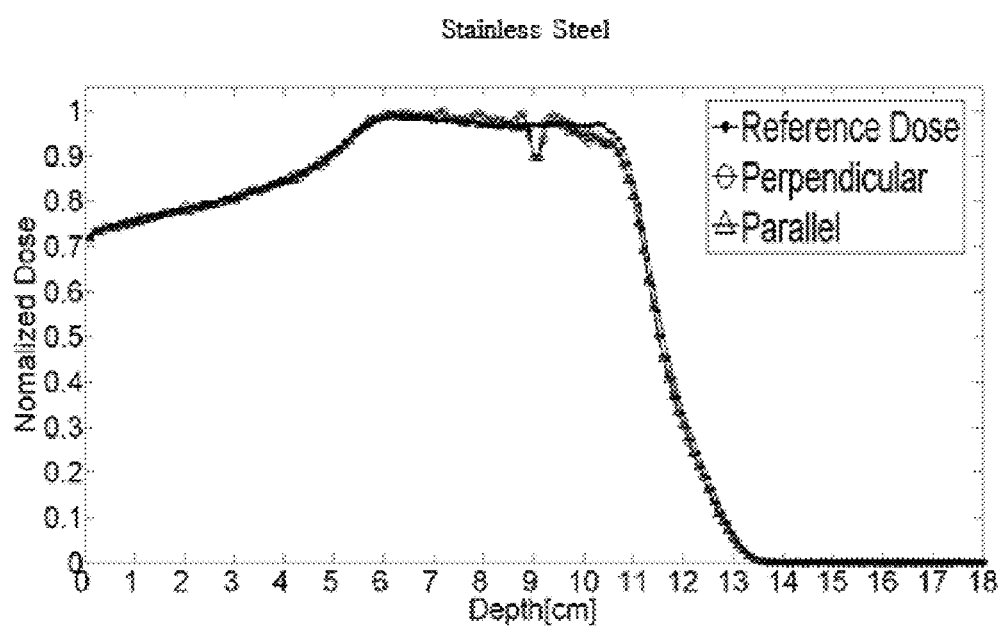
Figure 8C:
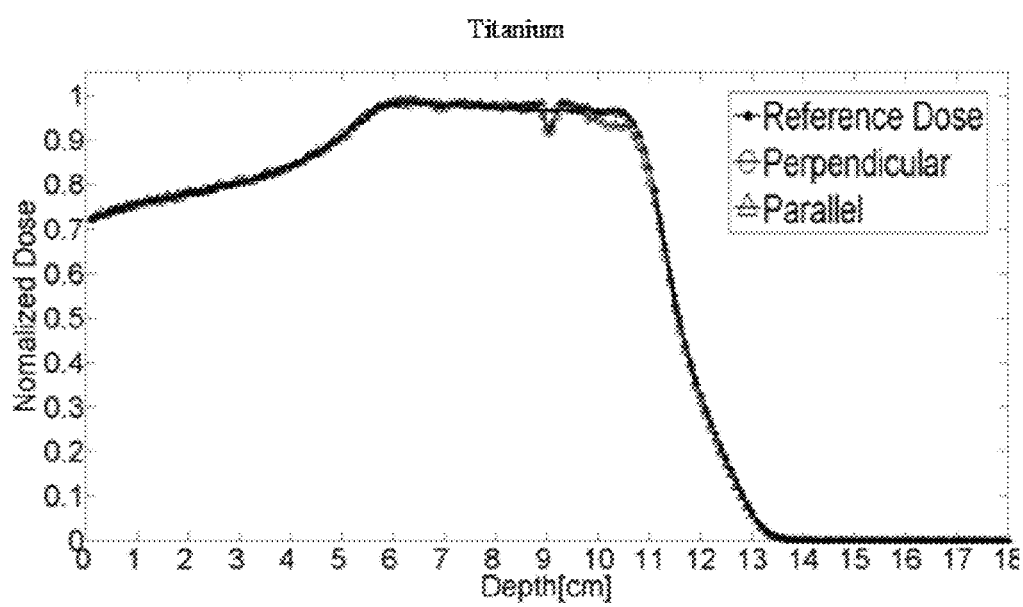
Figure 8D:
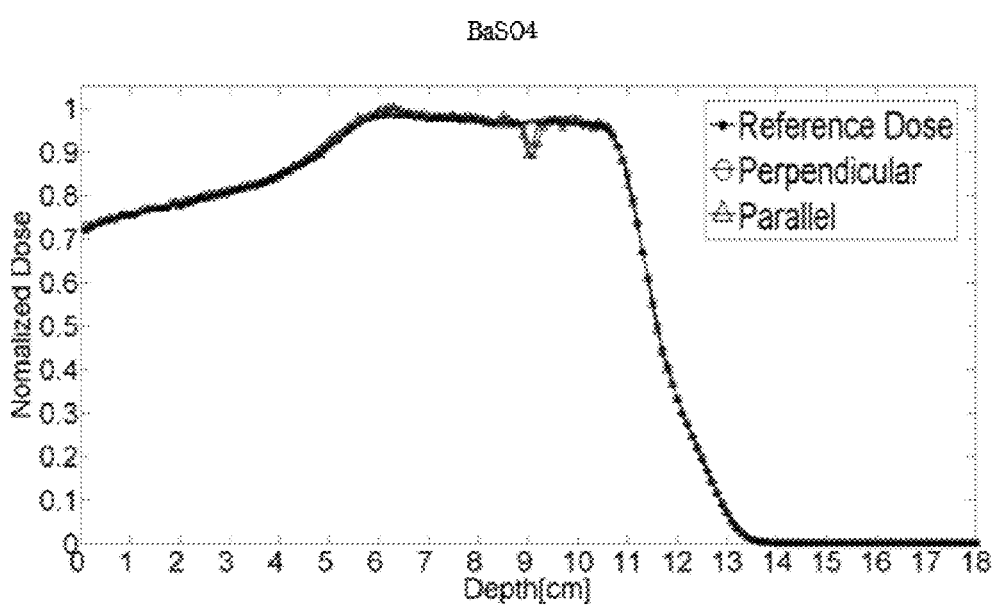

In order to quantitatively compare the size change of the barium sulfate (BaSO$_4$), any six mice (B1 1 mm 1 animal, 2 mm 2 animals, B2 1 mm 1 animal, 2 mm 2 animals) were selected, and the size changes thereof were compared on the cone-beam computed tomography (CBCT) D0 (imaging immediately after marker injection) image and D11 (last imaging) image MATLAB (Version R2012a, The Math Works, Inc, USA) was used to reconstitute an image in which the outline of the marker corresponding to the cone-beam computed tomography (CBCT) slice image of the barium sulfate (BaSO$_4$) marker, and then the image was made to have a 3D volume, of which voxels were then converted into volume values for comparison (table 2 and FIG. 6). The percent of volume reduction was 9.88% to 65.23%, and was not different between the barium sulfate (BaSO$_4$) 10 wt % (B1) and the barium sulfate (BaSO$_4$) 20 wt % (B2) according to the content of barium sulfate (BaSO$_4$).

TABLE 2

| Marker | Mouse | Size (mm) | D0 volume (cm$^3$) | D11 volume (cm$^3$) | (D0) − (D11) | Reduction (%) |
| --- | --- | --- | --- | --- | --- | --- |
| B1 | No. 5 | 1 | 0.0085 | 0.0060 | 0.0025 | 29.11 |
|  | No. 3 | 2 | 0.0160 | 0.0055 | 0.0105 | 65.23 |
|  | No. 1 | 2 | 0.0235 | 0.0138 | 0.0097 | 41.24 |
| B2 | No. 6 | 1 | 0.0072 | 0.0044 | 0.0028 | 39.67 |
|  | No. 8 | 2 | 0.0223 | 0.0201 | 0.0022 | 9.88 |
|  | No. 2 | 2 | 0.0208 | 0.0179 | 0.0029 | 13.43 |

Image Distortion Evaluation Results-Area Histogram Analysis

In order to evaluate the degree of image distortion of the barium sulfate (BaSO$_4$) marker, the degree of image distortion was compared between the barium sulfate (BaSO$_4$) marker and the gold marker. B1 marker, B2 marker, and a gold marker commercialized product (Gold marker, diameter: 1 mm, length: 3 mm, CIVCO, USA) were housed inside the polymethacrylicacidmethyl (PMMA) phantom, and the image acquisition condition values (300 mA, 120 kV, slice thickness 1.25 mm, 512×512 pixels) were set, and computed tomography (CT) imager (LightSpeed RT 16, GE Healthcare, USA) was used for imaging. The region of interest (ROI) image in the coronal direction, on which B1 marker, B2 marker, and the gold marker were placed, were set to 20×20 pixels (15.6×15.6 mm$^2$), and then the degree of image distortion was analyzed by the histogram for two-dimensional analysis. For accurate comparison and analysis, the area of each marker was excluded, and for quantitative evaluation, the mean value and standard deviation value of Hounsfield unit (HU) were analyzed.

The Hounsfield Unit (HU) number around the gold marker has a mean value of 93.31 and a variance value of 5.53×10$^4$; the Hounsfield Unit (HU) number around B1 marker had a mean value of 148.95 and a variance value of 3.01×10$^3$; and the Hounsfield Unit (HU) number around B2 marker had a mean value of 155.67 and a variance value of 2.53×10$^3$. With respect to comparison of variance distribution, the gold marker was different from B1 marker and B2 marker by about 20 fold. This shows that the degree of image distortion in the periphery of a marker was more serious in the gold marker than B1 marker and B2 marker.

Such image distortion of the gold marker makes it difficult to differentiate the tumor tissue from the surrounding normal tissues, thereby increasing the inaccuracy in creating the accurate therapy plan. Therefore, the use of the barium sulfate (BaSO$_4$) marker of the present invention for radiotherapy minimizes the image distortion, thereby differentiating the tumor tissue from the surrounding normal tissues more clearly, and thus can help creating the accurate therapy plan.

Monte Carlo Simulation Dose Distortion Results

The gold marker showed dose distortion of −15.05% in a parallel direction and −9.77% in a perpendicular direction; the stainless steel marker showed dose distortion of −7.92% in a parallel direction and −4.43% in a perpendicular direction; and the titanium marker showed dose distortion of −6.92% in a parallel direction and −0.78% in a perpendicular direction. The barium sulfate (BaSO$_4$) marker showed a dose distortion result of −3.79% in a parallel direction and −0.53% in a perpendicular direction. Such results were similar to or lower than those of stainless steel and titanium, which showed lower degrees of dose distortion (FIG. 8a to FIG. 8d). Therefore, the use of the barium sulfate (BaSO$_4$) marker as a radiotherapy marker can reduce the dose distortion due to the marker at the time of radiotherapy, and thus can help in treating patients at a planned therapeutic dose.

Features and advantages of the present invention are summarized as follows.

(i) The present invention relates to a fiducial marker comprising barium sulfate (BaSO$_4$), a solvent, and a polyethylene glycol-poly(aminoureaurethane) multi-block copolymer, as active ingredients.

(ii) The fiducial marker of the present invention has an effect of significantly solving disadvantages of image distortion and dose distortion, which are involved in the gold inner marker used in the conventional art.

(iii) The fiducial marker of the present invention has very limited in vivo mobility, and thus the fiducial marker is maintained at the position at which it has been initially injected into the body.

(iv) Since the fiducial marker of the present invention is maintained in a sol or liquid phase before in vivo injection, and transited into a gel or solid phase after in vivo injection, the injectability of the fiducial marker by an injector syringe is favorable, and the phase of the fiducial marker can be controlled into a phase suitable to each site of the therapeutic target.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A fiducial marker, comprising: (i) barium sulfate (BaSO$_4$); (ii) a solvent; and (iii) a polyethyleneglycol-poly(aminoureaurethane) multi-block copolymer, as active ingredients, wherein the content of the barium sulfate (BaSO$_4$) is 10-20 wt %, wherein the content of the polyethyleneglycol-poly(aminoureaurethane) multi-block copolymer is 1-20 wt %, and wherein the polyethylene glycol-poly(aminoureaurethane) multi-block copolymer has a repeat unit represented by chemical formula 1 below:

[Chemical Formula 1]

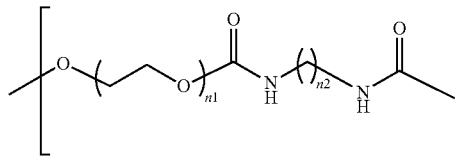

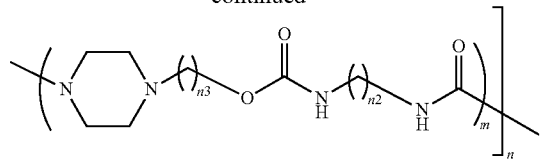

wherein n1 is an integer of 7 to 50;

n2 is an integer of 2 to 8;

n3 is an integer of 1 to 10; and m is an integer of 2 to 6.

2. The fiducial marker of claim 1, wherein the polyethylene glycol-poly(aminoureaurethane) multi-block copolymer has a molecular weight of 15,000 g/mol to 25,000 g/mol.

3. The fiducial marker of claim 1, wherein in chemical formula 1, n2 is 6.

4. The fiducial marker of claim 1, wherein in chemical formula 1, n3 is 2.

5. The fiducial marker of claim 1, wherein the solvent is a buffer.

6. The fiducial marker of claim 5, wherein the buffer is buffered saline.

7. The fiducial marker of claim 1, wherein the fiducial marker is used to display the position of a diseased part in the body at the time of radiotherapy.

8. The fiducial marker of claim 1, wherein the polyethylene glycol-poly(aminoureaurethane) multi-block copolymer is degraded in vivo.

9. The fiducial marker of claim 1, wherein the fiducial marker is in an injection type in which the fiducial marker is injected into the body in a sol phase.

10. The fiducial marker of claim 1, wherein the fiducial marker is hardened in a gel phase in the body after in vivo injection.

11. The fiducial marker of claim 1, wherein the fiducial marker shows a 90% or more reduction in the degree of image distortion compared with a metal fiducial marker.

12. The fiducial marker of claim 1, wherein the fiducial marker shows a 11.26% or more reduction in the degree of dose distortion compared with a metal fiducial marker.

* * * * *